United States Patent [19]

Wong

[11] Patent Number: 4,629,449
[45] Date of Patent: Dec. 16, 1986

[54] VAGINAL DISPENSER FOR DISPENSING BENEFICIAL HORMONE

[75] Inventor: Patrick S. Wong, Hayward, Calif.
[73] Assignee: ALZA Corporation, Palo Alto, Calif.
[21] Appl. No.: 714,421
[22] Filed: Mar. 21, 1985

Related U.S. Application Data

[62] Division of Ser. No. 402,953, Jul. 29, 1982, abandoned.
[51] Int. Cl.$^4$ .................................... A61M 31/00
[52] U.S. Cl. ............................ 604/55; 604/49; 604/54; 604/890; 604/892; 604/285; 424/19
[58] Field of Search ................ 128/127, 130; 424/DIG. 7, 15, 14, 16, 19, 31; 604/890, 892, 99, 893, 54–56, 285, 288

[56] References Cited

U.S. PATENT DOCUMENTS

| | | | |
|---|---|---|---|
| 3,545,439 | 12/1970 | Duncan | 3/36 |
| 3,797,492 | 3/1974 | Place | 128/260 |
| 3,828,781 | 8/1974 | Rothman | 128/278 |
| 3,896,819 | 7/1975 | Zaffaroni et al. | 128/130 |
| 3,938,515 | 2/1976 | Leeper et al. | 128/260 |
| 3,991,760 | 11/1976 | Drobish et al. | 128/260 |
| 3,995,633 | 12/1976 | Gougeon | 128/260 |
| 3,995,634 | 12/1976 | Drobish | 128/260 |
| 4,155,991 | 5/1979 | Schopflin et al. | 128/130 |
| 4,198,634 | 4/1980 | Drobish et al. | 128/260 |
| 4,215,691 | 8/1980 | Wong | 128/260 |
| 4,237,885 | 12/1980 | Wong et al. | 128/260 |
| 4,265,236 | 5/1981 | Pacella | 128/203 |
| 4,292,965 | 10/1981 | Nash et al. | 128/127 |
| 4,326,510 | 4/1982 | Buckles | 128/127 |

OTHER PUBLICATIONS

"The Role of Estrogen/Progestogen in the Management of the Menopause", ed. Cooke, Chapter 5, Whitehead et al.; MTP Press, Lancaster, England; 1978; pp. 63–75.
"Ov. Fail and Age", Studd; *Clin. Endrocrinol. Metab.;* 1981; pp. 89–113, vol. 10(1), [Chem Abst. 95:91228f].
*Textbook of Gynecology*, Chapter 12, pp. 209–215, 1977, Edited by Russell Ramon De Alvarez, M. D.
*Modern Trends*, "The Menopause: Benefits and Risks of Estrogen–Progestogen Replacement Therapy", vol. 37, No. 4, Apr. 1982, R. Don Gambrell, Jr., M. D.

*Primary Examiner*—Richard J. Apley
*Assistant Examiner*—Gregory Beaucage
*Attorney, Agent, or Firm*—Paul L. Sabatine; Edward L. Mandell; Steven F. Stone

[57] ABSTRACT

The invention is for a method of treating a decrease in estrogen secretion in a woman after the cessation of cyclic ovulation using a vaginal dispenser comprising a wall surrounding an internal lumen and having a pair of ends with one end placed inside the other end to form a closed dispenser. A vaginally administrable beneficial agent is housed in the lumen for release by the dispenser over time.

6 Claims, 2 Drawing Figures

VAGINAL DISPENSER FOR DISPENSING BENEFICIAL HORMONE

CROSS-REFERENCE TO RELATED APPLICATION

This application is a division of U.S. patent application Ser. No. 06/402,953 filed Jul. 29, 1982, now abandoned.

FIELD OF THE INVENTION

This invention pertains to a vaginal dispenser. More specifically, the invention relates to an intravaginal dispenser housing a vaginally dispensable drug for dispensing to a vagina over a prolonged period of time.

BACKGROUND OF THE INVENTION

Vaginal devices for delivering a drug to a vagina are known to the prior art. For example, U.S. Pat. No. 196,979 issued to patentee R. H. Kline, discloses a medicated-ring device consisting of a fabric filled with a medicinal agent useful for treating vaginal diseases. In U.S. Pat. No. 3,545,439 issued to Gordon W. Duncan there is disclosed an intravaginal ring-shaped device that can be made of various kinds of polymeric materials. The device is formed of a solid polymer containing drug that is released by diffusion to the vagina. The device optionally contains a tension spring for keeping it in the vagina. In U.S. Pat. No. 3,920,805 patentee Theodore J. Roseman discloses a solid polymeric device that has a non-medicated central solid core and an encircling medicated coating on the polymer. The device releases drug by diffusion and in a preferred embodiment, the device is ring-shaped with a flat tensioning spring molded in the nonmedicated central core. A vaginal medicament dispensing means is disclosed by James Lee Drobish and Thomas William Gougeon in U.S. Pat. No. 3,991,760. The device in this patent consists of a plurality of containers having walls releasably containing an active agent and connected by a fin arrangement. A vaginal medicament dispensing device is disclosed in U.S. Pat. No. 3,995,633 by patentee Thomas W. Gougeon. The device is characterized by a plurality of containers held in place by a retaining ring by virtue of their bulbous shape. U.S. Pat. No. 4,012,496 issued to Gisela Schopflen et al discloses a vaginal ring consisting essentially of a supporting medicament-free vaginal ring having an encircling indentation with a smaller vaginal medicament containing anular ring in the indentation. U.S. Pat. No. 4,155,991 issued to Gisela Schopflin et al is similar to U.S. Pat. No. 4,012,496 reciting the structure and additionally the polymer used for making the vaginal ring. A vaginal contraceptive system is described in U.S. Pat. No. 4,215,691 issued to Patrick S. Wong. The vaginal system comprises a wall surrounding a reservoir housing a drug and a carrier and made of a copolymer. U.S. Pat. No. 4,292,964 issued to Harold A. Nash et al disclosed an intravaginal ring consisting essentially of an inner core, a medicated layer encircling the inner core, and an outer layer surrounding the medicated layer. In U.S. Pat. No. 4,286,587 patentee Patrick S. Wong discloses a vaginal device comprising a delivery module with an internal reservoir housing a drug for controlled release to a vagina.

The vaginal devices described above are useful for their intended purpose and they represent a valuable contribution to the vaginal dispensing art. Now, it has been discovered a vaginal dispenser can be provided that is easy to manufacture, can be made with materials that are vaginal acceptable and can be used for dispensing drug to the vagina over time. The present invention provides an improvement by making available a vaginal dispenser manufactured as a closed dispenser from the materials comprising the vaginal dispenser.

BRIEF DESCRIPTION OF DRAWINGS

In the drawings, which are not drawn to scale, but are set forth to illustrate various embodiments of the invention, the drawing figures are as follows.

In the drawings and in the specification, like parts in related Figures are identified by like numbers. The terms appearing earlier in the specification, and in the description of the drawings, as well as embodiments thereof, are further described elsewhere in the disclosure.

DETAILED DESCRIPTION OF THE DRAWINGS

Figure 1:
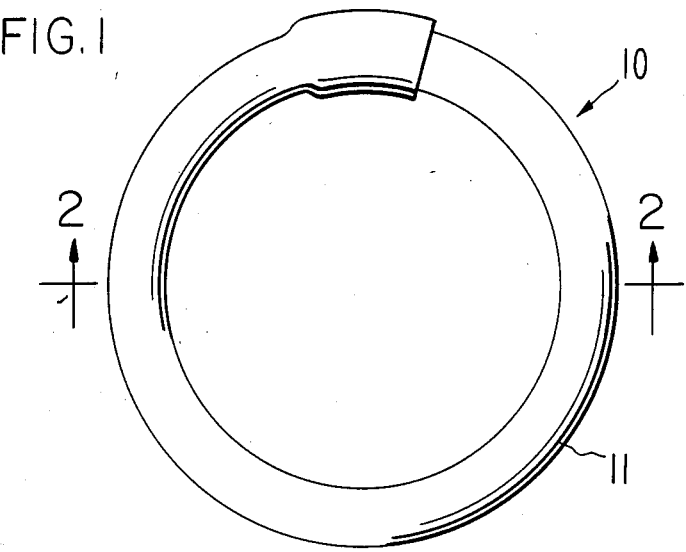
FIG. 1 illustrates an intravaginal dispenser sized, shaped and adapted for easy insertion and comfortable retention in a vagina; and, FIG. 2 illustrates the intravaginal dispenser of FIG. 1 seen in opened section through 2—2 of FIG. 1.

Turning now to the drawings in detail, which are an example of an intravaginal dispenser that can be used for delivering a vaginally acceptable drug to a vagina, and which example is not to be construed as limiting the invention, one presently preferred embodiment thereof is seen in FIG. 1 and identified by the numeral 10. In FIG. 1, vaginal dispenser 10 comprises a body 11 sized, shaped and adapted for placement in a vagina.

Figure 2:
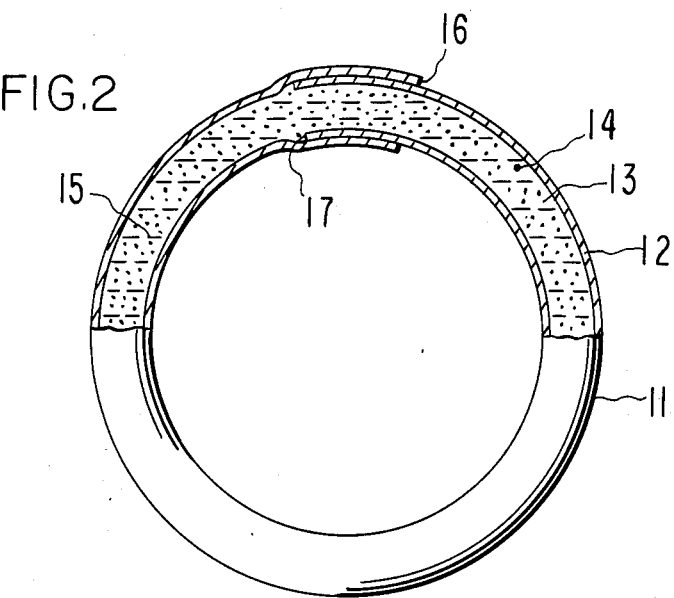

In FIG. 2, vaginal dispenser 10 is seen in opened section through 2—2 of FIG. 1. In FIG. 2, vaginal dispenser 10 is seen comprising body 11 formed of wall 12 formed of a polymer that releases a vaginally acceptable agent by diffusion, or wall 12 is formed of a microporous polymer that releases a vaginally acceptable agent through its micropores, and which rate in either instance maintains the prescribed rate of vaginally acceptable useful agent to the vagina throughout the life of vaginal dispenser 10. Wall 12 surrounds and forms an internal reservoir 13 for storing beneficial agent 14, represented by dots. Reservoir 13 also contains a carrier for agent 14, which carrier is an inner mass transfer conductor for supplying agent 14 to wall 12. Wall 12 surrounding internal reservoir 13 comprises a pair of ends, end 16 and end 17, that are joined into a single, integral shaped tubular vaginal dispenser 10. The union is effected by enlarging end 16 for slidably receiving end 17 in mated relation to form an essentially fluid tight union. In another embodiment, vaginal dispenser 10 can have at least one of ends 16 or 17 made smaller than the other end and the smaller end placed in the non-enlarged end to form a closed vaginal dispenser 10.

Vaginal dispenser 10 can embrace many shapes, and in a presently preferred embodiment it comprises a single annular shape, which annular shapes include ring, oval, ellipse, toroidal, and like appearing annular shapes. The novel vaginal dispenser 10 can be used for delivering beneficial agent 14 to animals, including warm-blooded mammals, which expression includes humans and primates. Vaginal dispenser 10 also can be used for delivering agent 14 to farm, laboratory, sport and zoo animals. The dimensions of the dispenser will vary depending on the host and the shape for delivering agent 14. For example, at its maximum dimension the dispenser wall measures from one loci on the wall to a distant loci on the wall of from 0.4 cm to 16 cm, with presently preferred dispensers exemplified by an annular shaped dispenser which can have an external diameter of from 0.5 cm to 14 cm, with general dimensions for various hosts as follows: humans 6 cm to 12 cm, sheep 2 cm to 7 cm, dogs 0.5 cm to 5.0 cm, swine 2 cm to 7.5 cm, household cats 0.4 cm to 4 cm, and dairy cattle 5 cm to 12 cm.

DETAILED DESCRIPTION OF INVENTION

In accordance with the practice of this invention, it has now been found vaginal dispenser 10 can be made with vaginally acceptable polymeric materials including polymeric materials that release agent 14 by diffusion and microporous polymeric materials that release agent 14 through its micropores. The polymeric materials used are substantially free of any adverse affects on the vagina and on the host. The vagina is lined with an extremely delicate tissue, and it is essential, therefore, that the materials forming dispenser 10 do not adversely affect the vagina. The materials used for the purpose of this invention are the vaginally compatible materials set forth below. By compatible is meant the materials are vaginally acceptable within the environment of the vagina and generally to the host. That is, these materials do not break down in the vagina, there is no absorption of the materials, there is no deleterious action on the sensitive tissues in the area of placement and retention of the vaginal dispenser over a prolonged period of time, and the materials do not harm the active agent and the carrier housed in dispenser 10.

The polymers suitable for the purpose of the invention mainly for forming wall 12 include polymers, copolymers and the like generically represented by olefin and vinyl-type polymers, carbohydrate-type polymers, condensation-type polymers, rubber-type polymers, and organosilicon polymers. In a presently preferred embodiment, one group of polymers useful for manufacturing vaginal dispenser are the polymers known as thermoplastic polymers. These polymers are capable of being softened by heating and hardened by cooling through a temperature range characteristic of the polymer, and in the softened state they can be shaped by flow into devices by molding or extrusion. The change for these materials upon heating is substantially physical. One example of a thermoplastic polymer that can be used for the present purpose is styrene-butadiene block copolymer. The styrene-butadiene block copolymer useful for manufacturing rate wall 12 includes those generally formed by initiation at a chain end of an already formed polymeric chain. The block copolymers are thermoplastic elastomers because of their ability to become fluid and moldable at elevated temperatures. These properties lend themselves to the manufacture of system 10. Generally, the styrene block copolymer will have a molecular weight in the range of 10,000 to 20,000 and the butadiene will have a molecular weight in the range of 40,000 to 100,000. Additional polymers that can be used for manufacturing dispenser 10 include poly(methylacrylate), poly(butylmethacrylate), plasticized poly(vinylchloride), plasticized nylon, plasticized soft nylon, plasticized poly(ethylene terephthalate), poly(ethylene), poly(acrylonitrile), poly(trifluorochloroethylene), poly(4,4'-isopropylene-diphenylene carbonate), poly(ethylenevinyl esters), poly(ethylenevinyl acetate), poly(vinyl chloridediethyl fumarate), poly(esters of acrylic and methacrylic), cellulose acetate, cellulose acylates, partially hydrolyzed poly(vinyl acetate), poly(vinyl butyral), poly(amides), poly(vinyl carbonate), poly(urethane), poly(olefins), and the like. These polymers and their physical properties are known to the art and they can be synthesized according to the procedures disclosed in *Encyclopedia of Polymer Science and Technology*, Vo. 15, pages 508 to 530, 1971, published by Interscience Publishers, Inc., New York; Polymers, Vol 17, 938 to 956, 1976; *Technical Bulletin SCR-159*, 1965, Shell Corp., New York; and references cited therein; and in *Handbook Of Common Polymers*, by Scott and Roff, published by CRC Press, 1971, Cleveland, Ohio.

The vaginal drug delivery dispenser as provided herein, can be manufactured from porous and microporous tubing made from polymers that can be melt extruded to form a tubular structure. In one process, a tube is produced from an extrudable polymeric composition, by extruding with a commerical extruder through a die, a polymer that includes a leachable additive of prepore forming size. Typical examples of leachable components are water soluble modified starches, and other water soluble polymers such a polyethylene oxides, polyethylene glycols, polyvinyl alcohol, sodium alignate, gelatin, hydroxyethyl cellulose, and the like. Leachable components can also be salts such as NaCl, KCl, NaHCO$_3$, Na$_2$CO$_3$, HaHPO$_4$ etc., or low molecular weight organic compounds such as urea, sorbitol, mannitol, fructose, etc.

In another process a polymer and a leachable sintered powder are mixed and extruded through a die of known shape and dimensions. A representative sintered powder is prepared by blending for example, hydroxypropyl cellulose and polyethylene glycol, followed by sintering the blend in a high speed mixture at an elevated temperature. Next a polymer and the powder are ground in a conventional grinder to a known sieve size. The blend is then extruded, and after extrusion the tube is subjected to intensive leaching or washing to produce a microporous structure in the tube wall. Another process for forming a porous tube comprises extruding in an extruder of a conventional type, and operated at a pressure needed for extrusion, a polymer and a blowing agent. Typical agents that create a foamed or a porous cellular structure include aryl-bissulfohydrazide, azodicarbonamide, azobisisobutyronitrile, ammonium sesquicarbonate, and the like. The blowing agent releases gas and expands when the tube is exposed to a heat zone, which physical action and evolution of gas forms the porous structure. Procedures, equipment and materials suitable for manufacturing porous and microporous structures are known to the art in U.S. Pat. No. 3,223,761 issued to Raley; in U.S. Pat. No. 3,551,538 issued to Yamamoto et al; in U.S. Pat. No. 3,552,658 issued to Thomas; in U.S. Pat. No. 3,911,072 to Saito et al; and in U.S. Pat. No. 4,182,582 to Youval et al.

The microporous polymeric material can further be described as having pores that can be characterized as continuous pores interconnected through tortuous paths of regular and irregular shape. Generally, the final microporous materials can possess from 5 to 95% with a pore size which permits controlled release of the drug. Generally a pore size of from 10 angstroms to 200 microns, or more can be used for releasing the agent, with the micropores filling with a carrier through which the agent migrates to the exterior of the dispenser. Materials useful for making microporous tubing includes the polymers described above and polymers such as polycarbonates, polyhexamethylene adipamide, polyolefins, polyalkylene sulfide, polyethers, polyesters, and like microporous homopolymers, copolymers and terpolymers.

Exemplary inner mass transfer carrier 15, include carriers that are suitable for housing drug 14 in reservoir 13, including solid, liquid, semi-liquid carriers and the like such as emulsions, gels, glycols, and the like. These carriers are permeable to the passage of drugs, they are capable of containing dissolved and undissolved drugs, and they are capable of forming a carrier wall interface at the inner surface of wall 12, such as a solid or a liquid carrier wall interface at the inner surface of wall 12. Typical carriers includes a member selected from the group consisting of mineral, animal, fruit, nut, plant, sylvan, inorganic and organic oils. The carriers also include a member selected from the group consisting essentially of liquids, glycols, alkylene glycols, dialkylene glycols, poly(alkylene glycols), poly-(oxyalkylene)-poly(oxyalkylene) copolymer, aqueous gels, and the like. The carriers also include aqueous carriers such as water, saline, and buffers. Representative of carriers include vegetable oil, aqueous media such as water mixed with poly(alkylene glycols) including poly(ethylene glycols) having a molecular weight of 400 to 6000, poly(propylene glycol) having a molecular weight of 500 to 2000, glycerol polysorbate 80, and the like. Representative solid carriers useful as the inner mass transfer conductor include gelatin, collagen, sodium alginate, gum tragacanth, and the like. The solid carrier in the reservoir can be also a thermosetting organopolysiloxane that is vulcanized with a peroxide curing catalyst such as benzol peroxide, di-p-chlorobenzol peroxide and the like at temperatures of about 200° C. and requiring a subsequent heat treatment. The solid carrier can be a hydroxyl terminated organopolysiloxane commonly known as room temperature vulcanizing elastomer polymers, RTV, which harden to carrier elastomers at room temperature after the addition of cross-linking agents in the presence of curing catalysts. Representative catalysts are metallic salts of carboxylic acids, such as tin salts, tin octoate, tin ethylhexanoate, and the like. The inner reservoir carrier can also embrace a single component silicone rubber composition cured at room temperature. The single component compositions contain primarily organopolysiloxanes with two terminal hydrolyzable acyloxy groups, such as an acetoxy group. The acyloxy groups are hydrolyzed to form trifunctional siloxane which crosslink the polymer into a cured carrier. The carrier can be formed also of a two component dimethylpolysiloxane composition, platinum catalyzed at room temperature or at slightly elevated temperature and capable of additional cross-linking. Silicone polymers are known in U.S. Pats. Nos. 2,541,137; 2,723,966; 2,863,846; 2,890,188; 2,927,907; 3,022,951 and 3,035,016; and Great Britain Pat. Nos. 798,669 and 804,199. Carriers are also known to the art in *Pharmaceutical Sciences*, by Remington, 1970, published by Mark Publishing Company, Easton, Penna.

The phrase beneficial agent as used herein denotes vaginally administrable physiologically active, or pharmacologically active substance that produces a local or a systemic effect when released in the biological vaginal environment. The useful active agent can be inorganic, or organic, a drug, a spermicide, a hormone, and the like.

The terms spermicide and spermicidal as used herein are intended to encompass agents that kill sperm, as well as those agents which immobilize or render sperm ineffective for their intended effect by their spermicide semen contact. In one embodiment the spermicides include anionic surface active spermicides, non-ionic surface active spermicides and cationic surface active spermicides, and mixtures thereof. Exemplary spermicides that can be released by vaginal dispenser 10 are represented by the following: di-isobutyl-phenoxypolyethoxy ethanol, dodecaethylene glycol monolaurate p-methanylphenyl polyoxyethylene, methoxypolyoxyethylene glycol laurate, nonylphenoxy-polyethoxy ethanol, polyethylene glycol of monoisooctyl phenol ether, polyoxyethylenenonyl phenol, polyoxyethylene nonylphenol ether, aminopropanesulfonate, nonylphenol nonaethoxylate, tri-isopropyl-phenoxypolyethoxy ethanol, sodium lauryl sulfate, glyceryl monoricinolate, spermicidal mixtures such as methoxypolyethylene glycol laurate and nonylphenoxypolyethoxyethanol, trioxymethylene and nonylphenoxypolyoxyethylene ethanol, p-triisopropyl-phenoxypolyethoxyethanol and sodium lauryl sulfate, p-diisobutyl-phenoxypolyethoxyethanol and nonylphenoxypolyethoxyethanol, sodium sulfodioctyl succinate and triisopropylphenyloxypolyethoxyethanol, glyceryl monoricinoleate and triisopropylphenyloxypolyethoxyethanol, and the like. The amount of spermicide in vaginal device 10 can be up to 100%. The amount of spermicide in the device, when the spermicide is mixed with a mass transfer conductor is about 0.5% to 80% by weight of the total ingredients in the vaginal dispenser. The dispenser, when in operation, releases a spermicidally effective amount of the spermicide over time, and more particularly from 50 microns to 500 milligrams per hour, or higher. The dispenser releasing the spermicide can be positioned prior to intercourse in the vagina, and removed in a period of time after intercourse, or the device can be inserted and maintained in the vagina for several days up to a month.

Vaginal dispenser 10 also can be used for estrogen replacement therapy, as related to ovarian functions. The cessation of ovarian function during middle life is a physiological event. It is medically accepted this event is the basis of the menopausal period. The menopausal period does not happen all at once, and this critical period of life that occurs in women is often referred to as the climacteric. The menopausal period is characterized by menopausal symptoms initiated by a decrease in estrogen secretion, which follows the cessation of cyclical ovulation and menstruation. The menopausal symptoms generally include hot flashes, fatigue, insomnia, obesity, wrinkles and emotional lability, and the postmenopausal osteoporosis or bone deterioration. It is generally recognized estrogen therapy, and estrogen in conjunction with progestin therapies, are useful for the management of the climacteric. The vaginal dispenser provide by the invention make available a method useful for relieving or preventing menopausal, perimenopausal, and postmenopausal symptoms. Exemplary extrogens useful for controlling the symptoms include estradiol, estradiol benzoate, estradiol cypionate, estradiol dipropionate, estradiol enanthate, conjugated estrogen, estriol, estrone, estrone sulfate, ethinyl estradiol, estrofurate, quinestrol, and mestranol. The amount of naturally occurring or synthetic estrogen in a device is from 5 milligrams to 2,500 milligrams or more, and it is released at a rate of 1 microgram to 7 milligrams per hour, per day, or longer.

Vaginal dispenser 10 also can be used for the control of ovulation, or the prevention of pregnancy by suppressing ovulation, by administering contraceptive hormones. The contraceptive hormones useful for this purpose include progestational and estrogenic hormones. The hormones when released into the vagina are absorbed into the body and are thought to prevent conception by inhibiting the release of luteinizing hormone-releasing factor from the hypothalmus. This physiological action prevents the follicle stimulating hormone from stimulating an ovarian follicle to grow, and it also prevents the luteinizing hormone from triggering ovulation.

The contraceptive hormones that are used for the program of the invention include broadly antifertility steriods that can be used for regulating the fertility or ovulatory cycle in females of reproduction age. The contraceptive hormones include progestational and estrogenic steriods. The term progestational steroid as used herein embraces progestogen, which term is used in the pharmaceutical art to generically describe steroids possessing progestational activity. The progestational steroids further include naturally occurring steroids and synthetic steroids known as progestins. Exemplary progestational steroids include progesterone or preg-4-ene-3,20-dione; 17α-hydroxy-progesterone or 17α-hydroxypregn-4-ene-3, 20-dione; 17α-hydroxy-progesterone 3-cyclopentyl enol; medrogestone or 6,17-dimethylpregna-4,6-diene-3,20-dione; medroxyprogesterone or 17α-hydroxy-6α-methylpregn-4-ene-3,-20-dione; megestrol acetate or 17α-hydroxy-6 methylpregna-4,6-diene-3,20-dione; chlormadione acetate or 6-chloro-17-α-hydroxypregna-4,6-diene-3, 20-dione acetate; allylestrenol or 17-(2-propenyl)ester-4-en-17-ol; ethynodiol or 19-nor-17α-pregn-4-en-20-yne-3α,17-diol; ethynodiol diacetate; lynestrenol or 19-nor-17α-pregn-4-en-20-yn-17-β-ol; norethindrone or 17-hydroxy-19-nor-17α-pregn-4-en-20-yn-3-one; norethynodrel or 17-hydroxy-19-nor-17α-pregn-5(10)-en-20-yn-3-one; norgestrel or 13-ethyl-17-hydroxy-18,19-dinor-17α-pregn-4-en-20-yn-3-one; norgesterone or 17-hydroxy-19-nor-17α-pregna-5(10), 20-dien-3-one; quingestrone or progesterone cyclopentyl-3-enol ether; and other progestins such as norvinesterone; levonorgestrel; oxogestone and tigestol. The estrogenic hormones used for controlling the ovulatory cycle include estradiol or estra-1,3, 5(10)-triene-3,17β-diol; estradiol 3-benzoate; estradiol 3-acetate; estradiol 3,17-diacetate; estriol or estra-1,3,5, (10)-triene-3, 16α-17β-triol; estrone or 3-hydroxy-estra-1,3,5-(10)-trien-17-one; ethinyl estradiol or 19-nor-17α-pregna-1,3,5 (10)-trien-20-yne-3,17-diol; mestranol or 3-methoxy-19-nor-17α-pregna-1,3,5(10)-triene-20-yn-17-ol; quinestradiol or 3-(cyclopentyloxy)-estra-1,3,5(10)-trien-16α-17β-diol; quinestrol or 3-(cyclopentyloxy)-19-nor-17α-pregna-1,3,5(10)-trien-20-yn-17-ol; and other estrogens, such as estrazinol; and estrofurate.

The administration of a contraceptive hormone, or the administration of a combination of contraceptive hormones in the vagina for entry into the systemic circulation, which act primarily through the mechanism of gonadotropin suppression due to the progestational and the estrogenic activities of the steroids, with the resulting inhibition of ovulation, can be effected by the programs provided by the invention. One program for administering the naturally occurring steroid progesterone to the vagina can be generically described as three-weeks-on and one-week off program. The program comprises the steps of (1) inserting the vaginal dispenser into the vagina on the fifth day of the menstrual cycle, counting the first day of bleeding as day one, (2) retaining the system in the vagina for 20 to 21 days, preferrably for three weeks, (3) administering from 1 microgram to 500 micrograms of progesterone to the vagina daily, preferrably into the vaginal fluid during the three week period, (4) removing the system from the vagina for one week, with no progesterone delivered during this period, and (5) repeating the contraceptive program at the end of this latter period by inserting a new delivery system into the vagina.

Another contraceptive program that can be used for the management of the ovulatory cycle comprises delivering progesterone to the vagina for one week from the fifth day to the twelfth day of the intermenstrual period. The system is positioned in the vagina beginning with day five of the menstrual period, counting the first day of bleeding as day one.

The contraceptive programs for delivering progestins to the vagina comprise delivering the hormonal steriod to the vagina preferrably to the vaginal mucosa, at the rate of 1 microgram to 2500 micrograms a day. The contraceptive programs presently preferred are the three-weeks-on and one-week-off, and the fifth to the twelfth day intermenstrual period programs as described above. The progestins include norethindrone, norethynodrel, norgestrel, and the like.

The contraceptive programs provided by the invention also include delivering a combination of a progestational and an estrogenic steroid to the vaginal environment. The program comprises inserting the vaginal dispenser into the vagina for releasing from 0.1 microgram to 3000 micrograms each at a continuous rate for three weeks of the four week cycle, or by using a program that corresponds to the oscillatory pattern exhibited by the normal ovarian cycle. Representative combinations that can be simultaneously released from the system include natural estrogen and natural progesterone; 35 mcg/day of ethinyl estradiol and 0.5 mg/day of norethindrone; 50 mcg/day of ethinyl estradiol and 1.0 mg/day of ethynodiol diacetate; 75 mcg/day of mestranol and 5.0 mg/day or norethyndrel; 30 mcg/day of ethinyl estradiol and 0.3 mg of norgestrel; 50 mcg/day of ethinyl estradiol and 0.5 mg of norethindrone; 80 mcg/day of mestranol and 1.0 mg of norethindrone; 50 mcg/day estrogen and 0.1 mg/day of progesterone; 100 mcg/day or estrogen and 0.4 mg/day or norethindrone; 40 mcg/day or estrogen and 0.5 mg/day of norgestrel; and the like. The vaginal dispenser houses from about 2 mcg of 5 grams of estrogenic steroid and about 2 mg to 5 grams of progestational steroid alone or in combination. The abbreviation mcg indicates microgram and mg indicates milligram, and /day indicates the rate of delivery per day. Generally, the progestational or the estrogenic contraceptive steroid will be released at the rate or 0.05 micrograms to 50 milligrams per day, excluding the specific contraceptive programs set fourth above. The steroids are known in *Remington's Pharmaceutical Sciences*, 14th Edition, 1970, published by Mack Publishing Company, Easton, Penna; and in *The Pharmacological Basis of Therapeutics*, by Goodman and Gilman, 4th Edition, 1970, published by MacMillian Company, London.

Additionally, the above progestational and estrogenic agents can be in the form of their pharmacologically accepted derivatives, such as their hydroxy or keto groups can be in a derivative form for the present purpose. The progestational or estorgenic derivative used should easily convert to the active agent upon its release from the device by biological activities such as enzymatic transformation, pH assisted hydrolysis in the vagina, tissue and metabolism and the like. The derivative can also be used to control the solubility of the agent in the carrier core and to assist in metering the agent from the device. Suitable derivatives include without limitation, esters with pharmaceutically acceptable acids such as acetate, glucuronate, benzoate, propionate, butyrate, valeroate, hexanoate, heptanoate, maleate, citrate, succinate, tartrate, fumarate, malate, ascorbate, sulphate, phosphate and the like; ethers such as lower alkoxy-tetrahydropyran-yl, unsubstituted tetrahydropyran-yl, silyl moieties, trifluoromethyloxy, cyclopentylenol ethers and other functional groups such as ureido, and the like.

The two ends joined in unity to define and form the vaginal dispenser can be held one within the other in fluid tight relation by solvent bonding, by adhesive joining, by heat fusing, by heat bonding, by pressure, and the like. When a solvent is used, the inside surface of one tube end that acts as a female member, and the outside surface of the other end that acts as a male member, are moistened with an organic solvent that causes the surfaces to feel tacky, and when placed in contact the surfaces then bond and adhere in a fluid tight union. The ends of the tube forming the body of the dispenser can be adhesively united to form a closed dispenser by applying an adhesive to the exterior surface of one end of the tube, and then slide the end into and against the inside surface of the other end. For the above procedures the solvents include organic solvents such as methylene chloride, ethylene dichloride, trichlorobenzene, dioxan, isophorone, tetrahydrofuran, aromatic and chlorinated hydrocarbons, mixed solvents such as 50/50 ethylene dichloride/diacetone alcohol; 40/60 alcohol/toluene; 30/70 alcohol/carbon tetrachloride, and the like. Suitable adhesives include natural adhesives and synthetic adhesives, such as animal, nitrocellulosic, polyamide, phenolic, amino, epoxy, isocyanate, acrylic, silicate, organic adhesives of polymers, and the like. The adhesives are known to the art in *The Encyclopedia of Chemistry*, Second Edition, edited by George L. Clark and Gessner G. Hawley, 1966, published by VanNostrand Reinhold Co., Cincinnati, Ohio; and the solvents are known in *Encyclopedia of Chemical Technology*, Kirk-Othmer, Sec. Ed., Vol. 16, 1969, published by Interscience, Publishers Inc., New York.

An intravaginal dispenser used for the purpose of this invention is manufactured as follows: first, a section of styrene-butadiene block copolymer vaginally acceptable tubing is washed with distilled water for 45 to 60 hours, and then dried in air at room temperature. Then, the tubing is cut into appropriate length and shaped like a ring as seen in FIG. 1, and molded into a torus at 165° C. Next, one end is enlarged by inserting a heated mandrel, cooled, and the outside of the other end of the tube very lightly dampened with methylene chloride and inserted into the female end for joining the opened tube at its ends, thereby forming a closed vaginal dispenser. Then, the hollow ring is filled by injecting a steroid carrier mixture into reservoir through a tube piercing inlet port pushed through the wall of the dispenser, with continuous filling of the reservoir until all the air is displaced through a tube piercing exit port also pushed through the wall of the dispenser. This procedure fills the reservoir. Finally, the piercing ports are removed, and the puncture points are sealed with a little methylene chloride. The reservoir is filled with progesterone in polyethylene glycol having a molecular weight of 400, at 5% wt/wt.

The procedure described above is repeated for preparing a vaginal dispenser having a toroidal shape and made with the same copolymer. The dispenser is manufactured from a length of clean tubing having a first end resiliently expanded for receiving the second end in a sealingly engaging relation to form a closed reservoir dispenser. The dispenser is made with a wall having a thickness of 1.78±0.08 mm, and internal diameter of 6 mm, and an outside diameter of 4.4 cms, and a reservoir containing 35% progesterone and 65% polyethylene glycol having a molecular weight of 600.

A vaginal dispenser useful for releasing a spermicide is manufactured as follows: first, a 16.5 cm length of a microporous cellulose tubing having a thickness when dry of 25 microns, and a thickness when wet of 50 microns is shaped like a ring. Then, one is permanently enlarged and the other end moistened with methylene chloride and the end inserted into the enlarged end, thereby joining the tube into a closed vaginal dispenser comprising a microporous wall surrounding and defining an internal, hollow reservoir. Next, the reservoir is filled by injecting into the reservoir nonylphenoxypolyethoxy ethanol, 30% by weight, in an aqueous carrier.

It will be understood to those versed in the art in the light of the present specification, drawings and the accompanying claims that the invention makes available to the art both a novel and useful vaginal device for delivering agents such as progestational and estrogenic steroids to produce a desired antifertility effect; and spermidices for their effects, the rate of release from these devices can be controlled to produce this effect, while simultaneously contributing to the dispensing art. It will be further understood to those versed in the art that different embodiments of this invention can be made without departing from the spirit and the scope of the invention. Accordingly, it is to be understood the invention is not to be construed as limited, but embraces all equivalents inherent herein.

I claim:

1. A method of treating a decrease in estrogen secretion in a woman exhibiting symptoms of a cessation of cyclical ovulation, which method comprises:
   (a) placing in the vagina of a woman exhibiting symptoms of a cessation of cyclical ovulation a dispenser adapted and shaped for easy placing and comfortable retention in the vagina, the dispenser comprising:
      (1) body means for housing and estrogen, which body means comprises a vaginally acceptable composition that is essentially-free of deleterious action on the vaginal tissues; and,
      (2) means in the dispenser for dispensing the estrogen from the dispenser over a prolonged period of time;
   (b) dispensing the estrogen from the dispenser into the vagina of said woman in a therapeutically effective amount for replacing estrogen and treating the decrease in said woman.

2. The method of treating a decrease in estrogen secretion in the woman in need of estrogen replacement according to claim 1, wherein the estrogen is a member selected from the group consisting of naturally occurring and synthetic estrogens.

3. The method of treating a decrease in estrogen secretion in the woman in need of estrogen replacement according to claim 1, wherein the estrogen is a member selected from the group consisting of estradiol, estradiol benzoate, estradiol cypionate, estradiol dipropionate, estradiol enanthate, conjugated estrogen, estriol, estrone, estrone sulfate, ethinyl estradiol, estrofurate, quinestrol and mestranol.

4. The method of treating a decrease in estrogen secretion in the woman in need of estrogen replacement according to claim 1, wherein the estrogen in the body means is present as a composition comprising an estrogenic and a progestational steroids.

5. A method for relieving the symptoms associated with menopausal, perimenopausal and post-menopausal periods in a woman having said periods and in need of estrogen therapy, which method comprises:
   (a) placing in the vagina of a menopausal, perimenopausal and postmenopausal woman a dispenser adapted and sized for easy placing and comfortable retention in the vagina, the dispenser comprising:
      (1) body means for housing an estrogen, which body means comprises a vaginally acceptable composition that is essentially-free of deleterious action on the vaginal environment; and,
      (2) means in the dispenser for dispensing the estrogen from the dispenser over a prolonged period of time; and
   (b) dispensing into the vagina from the dispenser the estrogen in a therapeutically effective amount for relieving the symptoms associated with menopausal perimenopausal and postmenopausal period in said woman.

6. A method for relieving the symptoms associated with the menopausal, perimenopausal and postmenopausal periods in a woman having said periods and in need of estrogen therapy, which method comprises:
   (a) positioning in the vagina of said woman a vaginal dispenser, said vaginal dispenser comprising:
      (1) body means for housing an estrogenic steroid, said body means comprising a non-toxic, vaginally acceptable, flexible polymeric composition shaped and sized for easy positioning and comfortable retention in the vagina over a prolonged period of time;
      (2) an estrogenic steroid useful for estrogen therapy in the dispenser present in an amount sufficient for relieving the symptoms;
      (3) releasing means in the dispenser for dispensing the estrogen from the dispenser over a prolonged period of time; and,
   (b) relieving the symptoms associated with the menopausal, perimenopausal and postmenopausal periods by delivering the estrogenic steroid in a therapeutically effective amount from the vaginal dispenser to the vagina to produce the intended therapy in said woman over a prolonged period of time.

* * * * *